United States Patent
Anda Fernandez et al.

(10) Patent No.: US 7,989,170 B2
(45) Date of Patent: Aug. 2, 2011

(54) **METHOD FOR THE DETECTION OF BACTERIAL SPECIES OF THE GENERA *ANAPLASMA/EHRLICHIA* AND *BARTONELLA***

(75) Inventors: Pedro Anda Fernandez, Madrid (ES); Horacio Gil Gil, Madrid (ES); Raquel Escudero Nieto, Madrid (ES); Isabel Jado Garcia, Madrid (ES); Isabel Rodriguez Moreno, Madrid (ES)

(73) Assignee: Instituto de Salud Carlos III, Madrid (ES)

( * ) Notice: Subject to any disclaimer, the term of this patent is extended or adjusted under 35 U.S.C. 154(b) by 0 days.

(21) Appl. No.: 12/648,928

(22) Filed: Dec. 29, 2009

(65) Prior Publication Data

US 2010/0129825 A1 May 27, 2010

Related U.S. Application Data (62) Division of application No. 11/954,708, filed on Dec. 12, 2007, now abandoned.

(51) Int. Cl.
*C12P 19/34* (2006.01)
*C07H 21/04* (2006.01)

(52) U.S. Cl. ................. 435/6.12; 435/91.2; 536/22.1; 536/24.33

(58) Field of Classification Search ..... 453/6; 435/91.2; 536/22.1, 24.33
See application file for complete search history.

(56) References Cited

U.S. PATENT DOCUMENTS

| 6,158,020 A | 12/2000 | Locker et al. |
| 6,300,072 B1 | 10/2001 | Jensen |
| 2008/0248473 A1* | 10/2008 | Fernandez et al. ............. 435/6 |

FOREIGN PATENT DOCUMENTS

| ES | 2264642 | 1/2007 |
| WO | 99/52370 | * 10/1999 |

OTHER PUBLICATIONS

Bekker et al. Vet. Microbiology, 2002, vol. 89, p. 223-238.*
Gundi et al. J. of Clinical Microbiology, vol. 42(8), 2004, p. 3816-3818.*
The nucleic acid sequence search reports for SEQ ID No: 26, 28-30, 32-33, 35-38.*
Lowe et al. Nucleic Acid Research, 1990, vol. 18(7), p. 1757-1761.*
Gonzalez et al. Appl. Environ. Microbiol. 1996, vol. 62(12). p. 4433-4444.*
Reubel et al. J. of Clinical Microbiology, 1998, vol. 36(6), p. 1501-1511.*
Alekseev et al. J of Clinical Microbiology, 2001, vol. 39(6), p. 2237-2242.*
Blaskovic D. et al., Oligo-chip based detection of tick-borne Bacteria, 2005 FEMS Microbiology Letters 243:273-8.
Anderson et al., J. Clin. Microbol. 1991, vol. 29912, pp. 2838-2842.

* cited by examiner

*Primary Examiner* — Kenneth R. Horlick
*Assistant Examiner* — Joyce Tung
(74) *Attorney, Agent, or Firm* — Leason Ellis LLP (57) ABSTRACT

The present invention relates to a method for the detection and identification of bacterial species belonging to the genera *Anaplasma/Ehrlichia* and *Bartonella*, and also provides triggers and probes required for its application, as well as associated kits.

4 Claims, 2 Drawing Sheets

METHOD FOR THE DETECTION OF BACTERIAL SPECIES OF THE GENERA *ANAPLASMA/EHRLICHIA* AND *BARTONELLA*

CROSS-REFERENCE TO RELATED APPLICATIONS

This application is a divisional of U.S. patent application Ser. No. 11/954,708, filed Dec. 12, 2007, which claims the benefit of priority to Spanish Patent Application No. ES 200701830, filed Jun. 29, 2007, both of which are hereby incorporated by reference in their entireties.

This application claims the benefit of priority to Spanish Patent Application No. ES 200701830, filed Jun. 29, 2007, which is hereby incorporated by reference in its entirety.

FIELD OF THE INVENTION

The present invention relates to a method for the detection and identification of bacterial species belonging to the genera *Anaplasma/Ehrlichia* and *Bartonella* (ES 2264642), and also provides triggers and probes required for its application, as well as associated kits.

BACKGROUND

To date, about 200 zoonotic diseases (e.g., bartonelosis, leptospirosis, Lyme borreliosis, etc.), which affect humans and represent one of the main causes of death and entail substantial economic loss in third world countries, have been described. Coexistence with animals, lack of sanitary infrastructure and low cultural level continue to be the main allies of these diseases.

In the same manner, certain types of zoonosis which are widespread in third world countries are now thriving in industrialized countries as a consequence of population increases in urban and periurban areas, and increased movement of animals across international borders. These circumstances, amongst others, entail the risk of introducing exotic diseases into the environment.

Additionally, the frequent findings of arthropods infected by more than one of the pathogens included in the present invention, increases the possibility of more than one zoonotic disease being transmitted in a single sting. As a result, hospitalizations due to medical profiles produced by contact with animals or arthropods, such as mosquitoes, ticks, fleas, lice, mites, etc., which act as vectors or pathogen reservoirs, is becoming increasingly common. Said medical profiles, due to their high degree of similarity, do not allow a fast and reliable identification of the pathogenous agent, so that specific and fast treatment is not possible and is occasionally administered too late. This undoubtedly justifies the need for a comprehensive method to detect and identify bacterial species that cause zoonosis.

To date, the molecular diagnosis methods available are basically limited to the detection of pathogens based on antibody technology. This type of analysis, generally retrospective and with low sensitivity levels, is normally of little use to treating diseases in acute-phase states.

Another alternative for the detection and identification of pathogens is based on the application of culture mediums. These types of techniques are scarcely applicable to certain species of genera, such as *Bartonella* and *Anaplasma/Ehrlichia*, due to the fact that said species do not normally grow in regular culture mediums and may even require cellular cultures. As a result, these methodologies are isolated from regular practice in hospital microbiology laboratories. One of the most effective alternatives to these types of methodologies is the direct analysis of genetic material, based on Polymerase Chain Reaction (PCR) technology. Said technology, while being highly effective, is greatly limited by the difficulty in finding specific markers or regions, in addition to triggers and probes, which ensure reliable sample analysis.

A paper has recently been published (Blaskovic D. et al. 2005. FEMS Microbiology Letters 243:273-8) which describes a method based on ribosomal DNA analysis, although it uses universal triggers which amplify the genetic material of both target and non-target bacteria, due to which its sensitivity is substantially reduced.

Other methods, such as those described by U.S. Pat. Nos. 6,300,072 and 6,518,020, are capable of detecting and identifying bacteria of the genus *Bartonella* by using the same region (16S-23S), even though the number of species within this genus has increased substantially since said patents were filed and their approximation, which consists of discriminating between species according to the size of the amplicon obtained during PCR, is not useful for certain known species within the same genus which are similar in size to the amplified fragment.

SUMMARY OF THE INVENTION

The present invention relates to the use of genes 16S and msp2 and intergenic space 16S-23S for the detection and identification of the different bacterial species and groups of species that cause zoonosis, improving the previously described procedures based on its capacity to specifically detect a substantial number of bacterial species using probes and triggers with high sensitivity levels.

Therefore, the present invention solves the problem of the tediousness and complexity of detecting a high number of bacteria that cause zoonosis which can be clinically and/or epidemiologically indistinguishable, through the development of a detection method and Kit based on PCR technology. Specifically, the invention allows the analysis of different regions of bacterial DNA belonging to the genera *Anaplasma/Ehrlichia* and *Bartonella* in order to identify both genus and species, as shown in the following table (Table 1).

In most cases, the species identified correspond to cultured species and, in others, correspond to species isolated for the first time (non-cultured species). Said species have been obtained from samples of *Meles meles* (badger), *Ixodes ricinus* and *Apodemus sylvaticus* species and have been characterized by the sequences AJ269792 and SEQ ID NO:44-46, as shown in Table 3.

TABLE 1

| BACTERIAL SPECIES | GENE |
|---|---|
| *Anaplasma/Ehrlichia* | |
| *A. phagocytophilum* msp2 | msp2 |
| *Ehrlichia ruminantium* | 16S |
| *E. sennetsu* | 16S |
| *E. risticii* | 16S |
| *E. muris* | 16S |
| *A. platys* | 16S |
| *E. canis/E. ovina* | 16S |
| *Bartonella* | |
| Generic | 16S |
| *B. talpae* | 16S-23S |
| *Bartonella* sp. * | 16S-23S |
| *B. phoceensis* | 16S-23S |
| *B. rattimasiliensis* | 16S-23S |
| *Bartonella* sp. detected in *Apodemus sylvaticus* | 16S-23S |

TABLE 1-continued

| BACTERIAL SPECIES | GENE |
| --- | --- |
| *B. rochalimae* | 16S-23S |
| *Bartonella* sp. detected in badger | 16S-23S |
| *Bartonella* sp ** detected in *Ixodes ricinus* | 16S-23S |
| *Bartonella* sp detected in *Ixodes ricinus* | 16S-23S |

* *B. chomeli/schoenbuchensis/capreoli/birtlesii*

DETAILED DESCRIPTION OF THE INVENTION

According to a first aspect of the invention, said invention relates to a method (hereinafter, method of the invention) for the detection and identification, preferably simultaneous, of any of the bacterial species and genera, as indicated in Tables 2 and 3, comprising the following steps:
a. Amplifying any of the sequences related to the group comprised of SEQ ID NO:1-17, 47 and/or their complementary sequences using specific triggers.
b. Detecting the amplification of the sequences mentioned in step a), said amplification being indicative of the presence or absence of the bacterial genera or species that cause zoonosis, as indicated in Tables 2 and 3.

The triggers required to apply the method of the invention may be designed by means of multiple alignment with the sequences comprising SEQ ID NO:1-17 and 47 using computer programs such as CLUSTAL X, and allow the identification of highly preserved regions that will act as a mould for trigger design, which must subsequently be validated empirically.

According to a preferred embodiment of this aspect of the invention, the triggers are capable of hybridizing with different nucleotide regions of the genes 16S, msp2 and intergenic space 16S-23S (Tables 2 and 3), although the sequences of said triggers shall preferably be selected from the SEQ ID NO:18-25 group and/or their complementary sequences, these being capable of amplifying SEQ ID NO:1-17, 47 and/ or their complementary sequences, in a preferably simultaneous manner. These triggers, in addition to simplifying the method, have the advantage of low or null reactivity with respect to samples of other species (see Table 5).

According to an even more preferred embodiment of this aspect of the invention, the detection of sequences SEQ ID NO:1-17, 47 and/or their complementary sequences may be carried out based on well-known methodologies within the art, preferably using probes. According to an even more preferred embodiment, said probes are capable of hybridizing between the positions of genes 16S, msp2 and intergenic space 16S-23S, as indicated in Tables 2 and 3, although said probes will preferably comprise the sequences selected from the group that comprises SEQ ID NO:26-42, 48 and/or their complementary sequences.

A second aspect of the invention relates to triggers capable of amplifying the sequences selected from the group comprising SEQ ID NO:1-17, 47 and their complementary sequences. Preferably, said triggers shall be capable of hybridizing between the nucleotide positions of genes 16S, msp2 and intergenic space 16S-23S, as indicated in Tables 2 and 3 (column 3). According to an even more preferred embodiment, the triggers comprise the sequences selected from the group SEQ ID NO:18-25 and/or their complementary sequences. Hereinafter, these will be referred to as triggers of the invention.

A third aspect of the invention relates to probes capable of specifically detecting any of the bacterial species and genera, as indicated in Tables 2 and 3 (column 6), said probes being capable of hybridizing between nucleotide positions of genes 16S, msp2 and intergenic space 16S-23S, as indicated in tables 2 and 3. According to an even more preferred embodiment, the probes have sequences selected from the group SEQ ID NO:26-47, 48 and/or their complementary sequences. Hereinafter, these will be referred to as probes of the invention.

A fourth aspect of the invention relates to an analysis kit for the identification of any of the bacterial genera or species, as indicated in tables 2 and 3, where said kit comprises any of the triggers or probes of the invention. Additionally, this kit may include all the reactive agents, buffers, supports, etc. required for its development, without limitation.

TABLE 2

Detection and identification of species belonging to the genera *Anaplasma/Ehrlichia*

| ORGANISM Anaplasma (Ehrlichia) | GENE | TRIGGER | PROBES | SEQUENCES | POSITION |
| --- | --- | --- | --- | --- | --- |
| A. phagocytophilum | msp2 | SEQ ID NO: 18 (EF143812 (1-22)) SEQ ID NO: 19 (EF143812 (313-334) | MSP2 (SEQ ID NO: 26) | SEQ ID NO: 1 | EF143812 (223-243) |
| Generic | 16S | SEQ ID NO: 20. (U02521 (9-30) SEQ ID NO: 21 (U02521 (109-86) | AEGEN (SEQ ID NO: 48) | SEQ ID NO: 47 | U02521 (38-57) |

TABLE 2-continued

Detection and identification of species belonging to the genera *Anaplasma/Ehrlichia*

| ORGANISM *Anaplasma* (*Ehrlichia*) | GENE | TRIGGER | PROBES | SEQUENCES | POSITION |
|---|---|---|---|---|---|
| *Ehrlichia ruminantium* | 16S | SEQ ID NO: 21 SEQ ID NO: 21 | S-RUM (SEQ ID NO: 27) | SEQ ID NO: 2 | DQ640401 (23-45) |
| *E. sennetsu* | 16S | SEQ ID NO: 20. SEQ ID NO: 21 | S-SEN (SEQ ID NO: 28) | SEQ ID NO: 3 | M73225 (46-63) |
| *E. risticii* | 16S | SEQ ID NO: 20. SEQ ID NO: 21 | S-RIS (SEQ ID NO: 29) | SEQ ID NO: 4 | AY005439 (46-65) |
| *E. muris* | 16S | SEQ ID NO: 20. SEQ ID NO: 21 | S-MUR (SEQ ID NO: 30) | SEQ ID NO: 5 | AY587608 (16-37) |
| *A. platys* | 16S | SEQ ID NO: 20. SEQ ID NO: 21 | S-PLA (SEQ ID NO: 31) | SEQ ID NO: 6 | EF139459 (53-75) |
| *E. canis/ E. ovina* | 16S | SEQ ID NO: 20. SEQ ID NO: 21 | S-CANOVIN (SEQ ID NO: 32) | SEQ ID NO: 7 | EF011111 (14-37) |

TABLE 3

Detection and identification of species belonging to the genus *Bartonella*

| ORGANISM *Bartonella* | GENE | TRIGGER | PROBES | SEQUENCES | POSITION |
|---|---|---|---|---|---|
| Generic | 16S | SEQ ID NO: 22 (AJ223780 (961-979)) SEQ ID NO: 23 (AJ223780 (1376-1398)) | BARTGEN2 (SEQ ID NO: 33) | SEQ ID NO: 8 | AJ223780 (1054-1075) |
| *B. talpae* | 16S-23S | SEQ ID NO: 24 (AY116638 (455-478)) SEQ ID NO: 25 (724-743 (AJ269786)) | S-TOPO (SEQ ID NO: 34) | SEQ ID NO: 9 | SEQ ID NO: 43 (90-113) |
| *B. phoceensis* | 16S-23S | SEQ ID NO: 24 SEQ ID NO: 25 | S-PHO (SEQ ID NO: 35) | SEQ ID NO: 10 | AY515123 (659-679) |
| *B. rattimasiliensis* | 16S-23S | SEQ ID NO: 24 SEQ ID NO: 25 | S-RAT (SEQ ID NO: 36) | SEQ ID NO: 11 | AY515122 (807-827) |
| *B. rochalimae* | 16S-23S | SEQ ID NO: 24 SEQ ID NO: 25 | S-ROC (SEQ ID NO: 37) | SEQ ID NO: 12 | AF415211 (414-434) |
| *Bartonella* sp. * | 16S-23S | SEQ ID NO: 24 SEQ ID NO: 25 | CHOSCA (SEQ ID NO: 38) | SEQ ID NO: 13 | AY116639 (438-461) |

TABLE 3-continued

Detection and identification of species belonging to the genus
*Bartonella*

| ORGANISM Bartonella | GENE | TRIGGER | PROBES | SEQUENCES | POSITION |
|---|---|---|---|---|---|
| Bartonella sp. in Apodemus sylvaticus | 16S-23S | SEQ ID NO: 24 SEQ ID NO: 25 | S-APO38 (SEQ ID NO: 39) | SEQ ID NO: 14 | AJ269792 (425-445) |
| Bartobella sp in Meles meles | 16S-23S | SEQ ID NO: 24 SEQ ID NO: 25 | S-TEJ (SEQ ID NO: 40) | SEQ ID NO: 15 | SEQ ID NO: 44 (329-350) |
| Bartonella sp. in Ixodes ricinus 13 | 16S-23S | SEQ ID NO: 24 SEQ ID NO: 25 | S-G-13 (SEQ ID NO: 41) | SEQ ID NO: 16 | SEQ ID NO: 45 (92-111) |
| Bartonella sp. in Ixodes ricinus 41 | 16S-23S | SEQ ID NO: 24 SEQ ID NO: 25 | S-G-41 (SEQ ID NO: 42) | SEQ ID NO: 17 | SEQ ID NO: 46 (86-104) |

* B. chomeli/schoenbuchensis/capreoli/birtlesii

Brief explanation of Tables 2 and 3:

Column 1 (organism) indicates the bacterial species or group of species detected in each case. The *Bartonella* sp. group refers to a group of species belonging to this genus with a high degree of similarity and which are jointly detected through a method of the invention.

Column 2 (gene) indicates the gene or genome region used to detect the bacterial species or group of species listed in column 1.

Column 3 (trigger) indicates the sequence of the pair of triggers required to amplify the variable regions of the gene or intergenic space indicated in each table (column 2), in addition to the sequence in which they hybridize.

Column 4 (probe) indicates the sequence of the probes used to detect the bacterial species or groups of species listed in column 1 of each table.

Column 5 (sequence 5'-3') indicates the references of the sequences of the variable regions which are amplified for the detection of each bacterial species or group of species.

Column 6 indicates the sequence code of a gene region or genome region listed in column 2, in addition to the specific position of each sequence in which the probe indicated in column 4 hybridizes.

DETAILED DESCRIPTION

The present invention has allowed the development of an analysis method for the detection and identification of different bacterial genera and species using PCR or Multiple PCR technology. Methodology development required the analysis of intergenic space 16S-23S rRNA of genes 16S and msp2. These regions were analyzed combining different software applications and by comparison in databases, until the candidate regions susceptible to being used to apply the method were detected.

Said candidate regions were used to create a large number of triggers and probes, most of which, approximately 90%, were rejected after hybridization testing, until those which did not develop crossed reactivity with samples of different origin (FIGS. 1 and 2, Table 5) and, additionally, had high sensitivity levels, were finally selected.

Below is a detailed description of the materials and methods used in the development of the present invention, in addition to representative examples thereof. These examples do not limit the invention, but rather illustrate it, demonstrating the efficiency of the method of the invention. The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the claims, along with the full scope of equivalents to which the claims are entitled.

EXAMPLES

Amplification, Hybridization, and Validation

This step includes the experimental analysis of the variable regions detected earlier using PCR for their validation. The isolated DNA was amplified using PCR, applying the following temperature cycle table and reaction mixture composition, together with the specific triggers used previously for said purpose.

| Temperature Cycles | | |
|---|---|---|
| Temperature (° C.) | Time | Cycles 25 |
| 94 | 9' | 1 |
| 94 | 15" | |
| 60 | 1' | 40 |
| 65 | 4' | |
| 65 | 7' | 1 |

PCR reaction mixture composition for a final volume of 50 μL:

| | |
|---|---|
| H₂O: | According to final DNA volume |
| Buffer Taq Gold LD: | 9 μL |
| Cl₂Mg [3 mM]: | 6 μL |
| dNTPs [200 mM]: | 1 μL × 4 |
| BSA [0.8 ug/uL]: | 4 μL |

-continued

| | |
|---|---|
| 14 specific Triggers (SEQ ID 1-2, SEQ ID 7-8, SEQ ID 25-26, SEQ ID 28-29, SEQ ID 31-32, SEQ ID 36-37, SEQ ID 52-53) [50 pm/μL]: | 0.5 μL of each (7 μL) |
| Taq Gold LD: | 0.5 μL [2.5 units] |
| Problem DNA: | maximum 800 ng |

The amplicons were sequenced for their validation, verifying that the amplified sequence coincided with the variable sequences inferred from bioinformatic studies.

Subsequently, the amplicons were hybridized with specific probes according to the Reverse Line Blotting (RLB) protocol described by Sjoerd G. T. Rijpkema et al., Journal of Clinical Microbiology, December 1995, p. 3091-3095, although applying the following modifications (FIGS. 1 and 2):

| | |
|---|---|
| Substrate: | Super Signal West Dura (Pierce, Ref: 34075) |
| Probes: | used with a concentration of between 0.2 and 3.2 picomoles/microliter |
| Incubation: | at 55° C. |
| Lavages: | at 52° C. |

Figure 1:
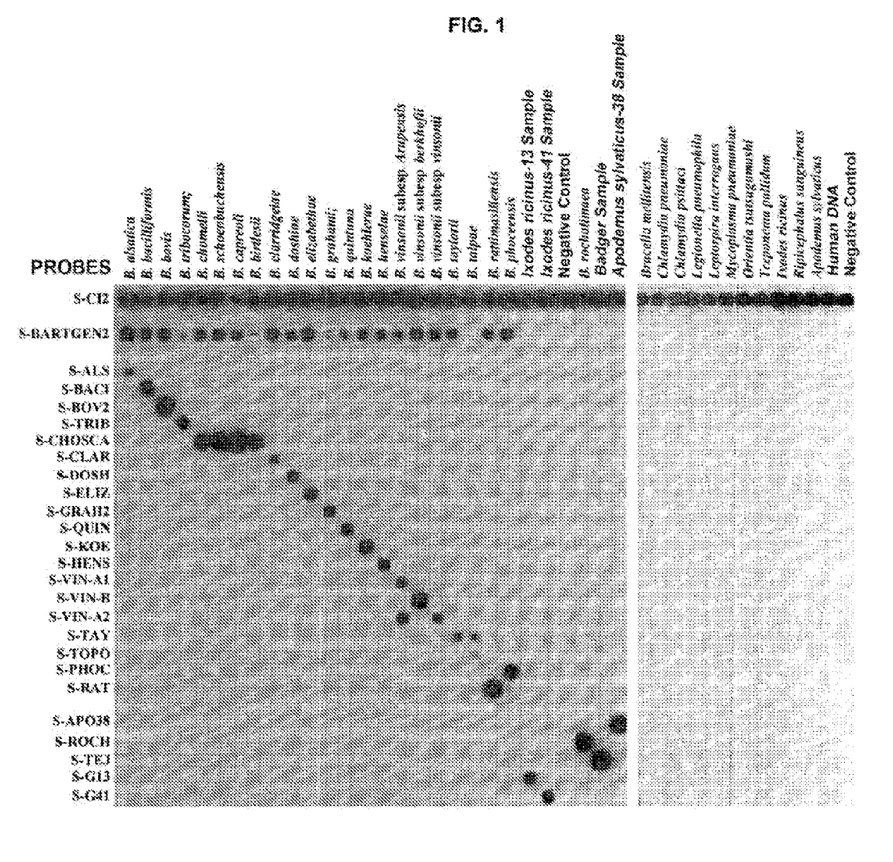
FIG. 1. This figure represents two hybridization membranes for the validation of triggers and probes used to detect the *Bartonella* genus. In the membrane on the left, the absence of crossed reactivity between the different probes within the genus is shown. In the membrane on the right, the absence of crossed reactivity in samples which do not contain the *Bartonella* genus is shown. The S-CI2 probe refers to the Internal Amplification Control (IAC) probe.
Figure 2:
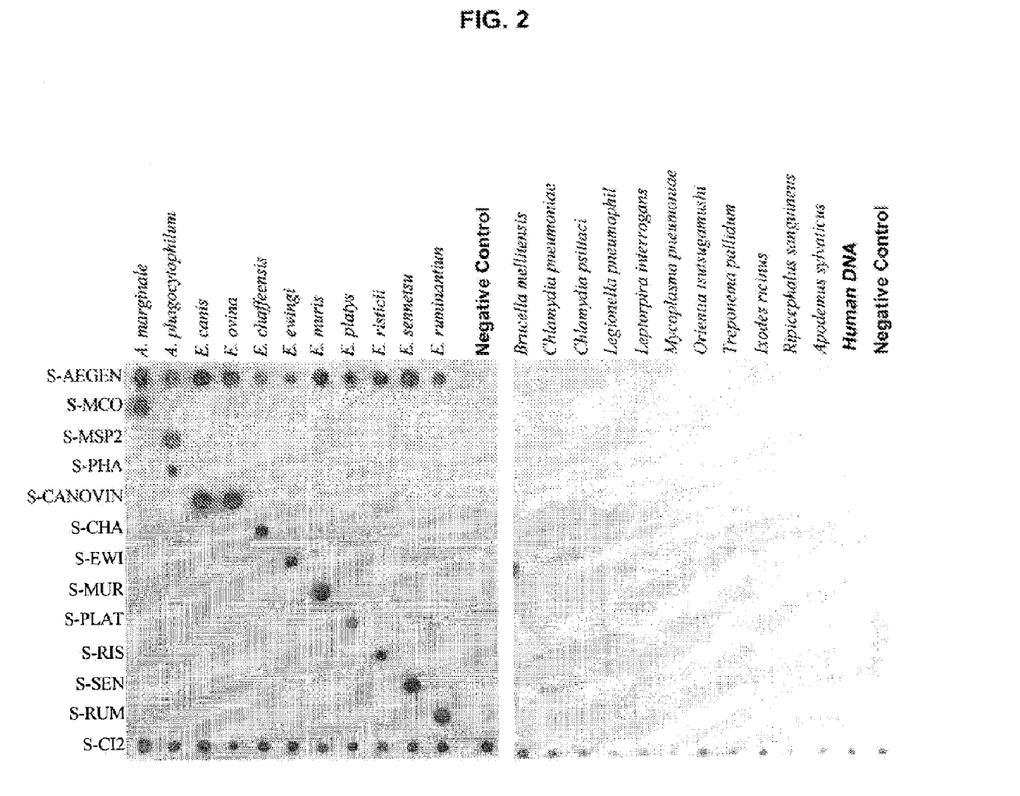
FIG. 2. This figure represents two hybridization membranes for the validation of triggers and probes used to detect the genera *Anaplasma/Ehrlichia*. In the membrane on the left, the absence of crossed reactivity between the different probes within the genus is shown. In the membrane on the right, the absence of crossed reactivity in samples which do not contain the genera *Anaplasma/Ehrlichia* is shown. The S-CI2 probe refers to the IAC probe.

Hybridization results are shown in FIGS. 1 and 2, where it is shown that each of the probes of the invention become joined specifically to each of the amplicons of the bacterial species detected using a method of the invention.

Preparation of Samples and Multiple PCR

One of the advantages of using PCR and RLB technology-based identification systems is that pure bacterial cultures are not required. In this manner and upon validation of the triggers and probes using DNA samples of the different species and subspecies listed in Tables 2 and 3, a Multiple PCR-based analysis of a DNA control mixture (FIGS. 1 and 2) prepared under laboratory conditions was carried out, followed by a RLB test, using the specifically designed triggers and probes and the previously indicated temperature cycles and reaction mixture composition.

Detection of PCR Inhibitors

An IAC, which was amplified together with target DNA, was created for the detection of PCR inhibitors, using specific triggers (Table 4) designed according to the preserved regions of the AB183705 sequence belonging to the THC synthase gene of the *Cannabis sativa* species. Specifically, the IAC amplicon corresponds to a sequence of 371 pairs of bases, for which a probe was also designed for detection during RLB.

TABLE 4

IAC. Amplified gene, sequence of each of the triggers and probes used in the process and their relative position.

| ORGANISM | GENE | TRIGGER | PROBES | SEQUENCE | POSITION 5'-3' |
|---|---|---|---|---|---|
| c. sativa | THC Synthase | SEQ ID NO: 51 (C1-F) | | | AB183705 (77-99) |
| | | SEQ ID NO: 52 (C1-R) | | | AB183705 447-427 |
| C. sativa | THC Synthase | SEQ ID 51 (C1-F) SEQ ID NO: 52 (C1-R) | SEQ ID NO: 50 (S-C12) | SEQ ID NO: 49 | AB183705 (281-302) |

Specificity of the Method

The high specificity of this method is based on the design and selection of the triggers and probes used, which were tested with another series of organisms (Table 5), following the previously described method, verifying that the formation of amplicons (FIGS. 1 and 2, right membrane) was in no case unspecifically detected.

TABLE 5

Specificity: unrelated bacterial, arthropod and mammal species used during method development.

| | SPECIES | RLB RESULT |
|---|---|---|
| | Bacteria | |
| 1 | *Brucella melitensis* | Negative |
| 2 | *Chlamydia penumoniae* | Negative |
| 3 | *Chlamydia psittaci* | Negative |
| 4 | *Legionella pneumophila* | Negative |
| 5 | *Leptospira interrogans* | Negative |
| 6 | *Mycoplasma pneumoniae* | Negative |
| 7 | *Treponema pallidum* | Negative |
| 8 | *Orientia tsutsugamushi* | Negative |
| | Arthropods | Negative |
| 9 | *Ixodes ricinus* | Negative |
| 10 | *Ripicephalus sanguineus* | Negative |
| | Mammals | Negative |
| 11 | *Apodemus sylvaticus* | Negative |
| 12 | Human | Negative |

All references cited and/or discussed in this specification are incorporated herein by reference in their entireties and to the same extent as if each reference was individually incorporated by reference.

We claim:

1. A method for detecting simultaneously bacterial species that cause zoonosis, belonging to the genera *Anaplasma/Ehrlichia* and *Bartonella*, comprising the following steps:
   a. placing a DNA sample under analysis in contact with a reaction mixture containing specific primers that will amplify one or more sequences from the gene msp2 and fragment 16S for *Anaplasma/Ehrlichia*, and from fragment 16S and 16S-23S for *Bartonella*
   b. amplifying the sequences by means of polymerase chain reaction;
   c. simultaneously detecting amplification products formed in the previous step by means of probes comprising SEQ ID NO: 26, SEQ ID NO: 28-30, SEQ ID NO: 32-33, and SEQ ID NO: 35-38, or their fully complementary sequences, used individually or in combination, said detection being indicative of the presence or absence of zoonosis-causing bacteria.

2. The method according to claim 1, further comprising the step of identifying the bacterial species corresponding to the amplification products.

3. The method of claim 2, wherein the steps of detecting and identifying are simultaneous.

4. A kit for detecting simultaneously bacterial species that cause zoonosis, belonging to the genera *Anaplasma/Ehrlichia* and *Bartonella*, comprising the probes SEQ ID NO: 26, SEQ ID NO: 28-30, SEQ ID NO: 32-33, and SEQ ID NO: 35-38, or their fully complementary sequences.

* * * * *

SEQUENCE LISTING

<160> NUMBER OF SEQ ID NOS: 52

<210> SEQ ID NO 1
<211> LENGTH: 21
<212> TYPE: DNA
<213> ORGANISM: Anaplasma phagocytophylum

<400> SEQUENCE: 1
ggtcttgaag cgctcgtaac c                                     21

<210> SEQ ID NO 2
<211> LENGTH: 23
<212> TYPE: DNA
<213> ORGANISM: Ehrlichia ruminantium

<400> SEQUENCE: 2
gccgargcta taataactg tcc                                     23

<210> SEQ ID NO 3
<211> LENGTH: 18
<212> TYPE: DNA
<213> ORGANISM: Ehrlichia sennetsu

<400> SEQUENCE: 3
gcaagcagct ttgattcc                                          18

<210> SEQ ID NO 4
<211> LENGTH: 20
<212> TYPE: DNA
<213> ORGANISM: Ehrlichia risticii

<400> SEQUENCE: 4
ctgcaagcag ccctgattcc                                        20

<210> SEQ ID NO 5
<211> LENGTH: 22
<212> TYPE: DNA
<213> ORGANISM: Ehrlichia muris

<400> SEQUENCE: 5
cgaacggata gctacccata gc                                     22

<210> SEQ ID NO 6
<211> LENGTH: 23
<212> TYPE: DNA
<213> ORGANISM: Anaplasma platys

<400> SEQUENCE: 6
catagcaagc tacgacaaaa atc                                    23

<210> SEQ ID NO 7
<211> LENGTH: 24
<212> TYPE: DNA
<213> ORGANISM: Ehrlichia canis

<400> SEQUENCE: 7
gccagaggct ataaataatt gtcc                                   24

<210> SEQ ID NO 8
<211> LENGTH: 22
<212> TYPE: DNA
<213> ORGANISM: Genus Bartonella

```
<400> SEQUENCE: 8
aatgctggca actaagggcg ag                                            22

<210> SEQ ID NO 9
<211> LENGTH: 24
<212> TYPE: DNA
<213> ORGANISM: Bartonela talpae

<400> SEQUENCE: 9
gattaaatgg acctaaaggg actg                                          24

<210> SEQ ID NO 10
<211> LENGTH: 21
<212> TYPE: DNA
<213> ORGANISM: Bartonela phoceensis

<400> SEQUENCE: 10
gagagacgct tttccctttg g                                             21

<210> SEQ ID NO 11
<211> LENGTH: 21
<212> TYPE: DNA
<213> ORGANISM: Bartonela rattimasiliensis

<400> SEQUENCE: 11
cggtgttttg aggcaaagtg c                                             21

<210> SEQ ID NO 12
<211> LENGTH: 21
<212> TYPE: DNA
<213> ORGANISM: Bartonela rochalimae

<400> SEQUENCE: 12
aacagggaaa agagcaggcc a                                             21

<210> SEQ ID NO 13
<211> LENGTH: 24
<212> TYPE: DNA
<213> ORGANISM: Bartonella sp.

<400> SEQUENCE: 13
cagcaaactt atcagcaatc ataa                                          24

<210> SEQ ID NO 14
<211> LENGTH: 21
<212> TYPE: DNA
<213> ORGANISM: Bartonella sp.

<400> SEQUENCE: 14 cctttctctcc tttttagggg c                                            21

<210> SEQ ID NO 15
<211> LENGTH: 22
<212> TYPE: DNA
<213> ORGANISM: Bartobella sp.

<400> SEQUENCE: 15
gatgttttgt aaaagtgcgt cg                                            22

<210> SEQ ID NO 16
<211> LENGTH: 20
<212> TYPE: DNA
<213> ORGANISM: Bartonella sp.
```

-continued

```
<400> SEQUENCE: 16
cgctcgtcta tcgcttgata                                              20

<210> SEQ ID NO 17
<211> LENGTH: 19
<212> TYPE: DNA
<213> ORGANISM: Bartonella sp.

<400> SEQUENCE: 17
gcaggcactc ggcataagc                                               19

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccagcgttta gcaagataag ag                                           22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcccagtaac aacatcataa gc                                           22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagaacgaac gctrgcggya rg                                           22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcrttackca cccgtctgcc ac                                           22

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccttcagttm ggctggatc                                               19
```

```
<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gccyccttgc ggttagcaca gca                                           23

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttgataagcg tgaggtcgga gg                                            22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caaagcaggt gctctcccag                                               20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
ggttacgagc gcttcaagac c                                             21

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
ggacagttat ttatagcytc ggc                                           23

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
ggaatcaaag ctgcttgc                                                 18

<210> SEQ ID NO 29
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
ggaatcaggg ctgcttgcag                                                     20

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
cgaacggata gctacccata gc                                                  22

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31 gattttgtc gtagcttgct atg                                                  23

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
ggacaattat ttatagcctc tggc                                                24

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33 ctcgcccttä gttgccagca tt                                                  22

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
cagtcccttt aggtccattt aatc                                                24

<210> SEQ ID NO 35
<211> LENGTH: 21
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 35
ccaaagggaa aagcgtctct c                                               21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
gcactttgcc tcaaaacacc g                                               21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
tggcctgctc ttttccctgt t                                               21

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
ttatgattgc tgataagttt gctg                                            24

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
gcccctaaaa aggagaaaag g                                               21

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
cgacgcactt ttacaaaaca tc                                              22

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 41
tatcaagcga tagacgagcg                                                   20

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
gcttatgccg agtgcctgc                                                    19

<210> SEQ ID NO 43
<211> LENGTH: 452
<212> TYPE: DNA
<213> ORGANISM: Bartonella talpae

<400> SEQUENCE: 43
ttgataagcg tgaggtcgga ggttcaagtc ctcccaggcc caccaattta cctatcccctt      60 tgcctttatc cgtttatttg ccgatttatc agtcccttta ggtccattta atcggtccat     120
ttataagtgt tggtaatagt ttttatcatg atggaaagtc atggttataa aagacctgct     180
tataaaactt ataaaaggct tgtttctaga ttgtgacgct tatccatttc gcttaggcaa     240
gagaaacttc aagcggtttg aaggcaaaat gctttgaatt ttgcaaaata atttgaattt     300
tgcaaaataa ttcaaatttt aaagtgatcc gattgaatct taaagtggat tgaattttaa     360
agtgatccaa gttcgtgatc tcgaatttaa aagtttcgaa tgctttatcc tttttttaggg    420 gccgtagctc agctgggaga gcacctgatt tg                                    452

<210> SEQ ID NO 44
<211> LENGTH: 427
<212> TYPE: DNA
<213> ORGANISM: Bartonella sp.

<400> SEQUENCE: 44
ttgataagcg tgaggtcgga ggttcaagtc ctcccaggcc caccaatcac actatgctga      60
aagctcctat gattgatcgc tttttgaata agcccttaaa ggaaatttat gatcttttat     120 aaaactttt cccttataaa actttataaa actttcttta tgaaacttta ttgtctcaga      180
gcattcagag agagtatgat atagcactca gaatatgata cagaaaacag agtatgagat    240
ataaagaacg tcacctctga aattgttttt ttatcatttt aaaagtctaa atattctgt      300 ctctattttt aattttaaa aagcatcaga tgtttttgtaa aagtgcgtcg ttttttatag     360
agcataacgt gaaagcattt taaactattt tagggccgt agctcagctg ggagagcacc     420
tgctttg                                                               427

<210> SEQ ID NO 45
<211> LENGTH: 201
<212> TYPE: DNA
<213> ORGANISM: Bartonella sp.

<400> SEQUENCE: 45
ttgataagcg tgaggtcgga ggttcaagtc ctccctggcc catttccttt agccccgggc      60
tagtagctca gttggttaga tcgaggagcg acgtcgtcg atcgcttgat aagcgtgagg     120
tcggaggttc aagtcctccc aggcccacca tattcctata ccttacgggg gcgtagctca    180

```
gctgggagag cacctgcttt g                                               201

<210> SEQ ID NO 46
<211> LENGTH: 186
<212> TYPE: DNA
<213> ORGANISM: Bartonella sp.

<400> SEQUENCE: 46
ttgataagcg tgaggtcgga ggttcaagtc ctcccaggcc caccactcca ttgcttacgc      60
acgtacgccc tttgggctgt gctgcgcagg cacgcggcat aagctgcgac ggccagtcgg     120
ccttgcgaag ctttgcttcg aatacctttta cggggggcgta gctcagctgg gagagcacct  180
gctttg                                                               186

<210> SEQ ID NO 47
<211> LENGTH: 21
<212> TYPE: DNA
<213> ORGANISM: Ehrlichia sp.

<400> SEQUENCE: 47
catgcaagtc gaacggatta t                                               21

<210> SEQ ID NO 48
<211> LENGTH: 21
<212> TYPE: DNA
<213> ORGANISM: Ehrlichia sp.
<220> FEATURE:
<221> NAME/KEY: modified_base
<222> LOCATION: (2)
<223> OTHER INFORMATION: inosine

<400> SEQUENCE: 48
andrkycgtt cgacttgcat g                                               21

<210> SEQ ID NO 49
<211> LENGTH: 22
<212> TYPE: DNA
<213> ORGANISM: Cannabis sativa

<400> SEQUENCE: 49
cctcctccac taaagtgtcc ac                                              22

<210> SEQ ID NO 50
<211> LENGTH: 22
<212> TYPE: DNA
<213> ORGANISM: Artificial Sequence
<220> FEATURE:
<223> OTHER INFORMATION: Description of the Artificial Sequence:
      Synthetic probe

<400> SEQUENCE: 50
gtggacactt tagtggagga gg                                              22

<210> SEQ ID NO 51
<211> LENGTH: 23
<212> TYPE: DNA
<213> ORGANISM: Artificial Sequence
<220> FEATURE:
<223> OTHER INFORMATION: Description of the Artificial Sequence:
      Synthetic primer

<400> SEQUENCE: 51
atgatgctga gggtatgtcc tac                                             23
```

```
<210> SEQ ID NO 52
<211> LENGTH: 21
<212> TYPE: DNA
<213> ORGANISM: Artificial Sequence
<220> FEATURE:
<223> OTHER INFORMATION: Description of the Artificial Sequence:
      Synthetic primer

<400> SEQUENCE: 52
gttttctcct ccaccaccac g                                              21
```